US012678537B2

(12) United States Patent
Chen et al.

(10) Patent No.: US 12,678,537 B2
(45) Date of Patent: Jul. 14, 2026

(54) FIBER MEMBRANE AND PREPARATION METHOD AND USE THEREOF

(71) Applicant: SHANGHAI RUIZHIKANG MEDICAL TECHNOLOGY CO., LTD., Shanghai (CN)

(72) Inventors: Xiaohong Chen, Shanghai (CN); Yubo Liu, Shanghai (CN); Honglei Zhou, Shanghai (CN); Wei Li, Shanghai (CN); Fengcang Ma, Shanghai (CN); Shaoli Fu, Shanghai (CN); Guosen Shao, Shanghai (CN); Haochen Wu, Shanghai (CN)

(73) Assignee: SHANGHAI RUIZHIKANG MEDICAL TECHNOLOGY CO., LTD., Shanghai (CN)

( * ) Notice: Subject to any disclaimer, the term of this patent is extended or adjusted under 35 U.S.C. 154(b) by 133 days.

(21) Appl. No.: 18/054,230

(22) Filed: Nov. 10, 2022

(65) Prior Publication Data

US 2024/0066182 A1 Feb. 29, 2024

(30) Foreign Application Priority Data

Aug. 24, 2022 (CN) .......................... 202211015904.2

(51) Int. Cl.
| | |
|---|---|
| *A61L 27/26* | (2006.01) |
| *A61L 27/12* | (2006.01) |
| *D01D 5/00* | (2006.01) |
| *D01F 1/10* | (2006.01) |
| *D01F 8/14* | (2006.01) |

(52) U.S. Cl.
CPC .............. *A61L 27/26* (2013.01); *A61L 27/12* (2013.01); *D01D 5/0038* (2013.01); *D01F 1/10* (2013.01); *D01F 8/14* (2013.01); *A61L 2300/216* (2013.01); *A61L 2430/02* (2013.01); *D10B 2331/041* (2013.01); *D10B 2509/00* (2013.01)

(58) Field of Classification Search
None
See application file for complete search history.

(56) References Cited

U.S. PATENT DOCUMENTS

2022/0186416 A1* 6/2022 Chen .................. D04H 1/43914

FOREIGN PATENT DOCUMENTS

CN 110195294 A 9/2019

OTHER PUBLICATIONS

Wang, Y., et al., Materials Science & Engineering C 98: 134-139 (2019). (Year: 2019).*
Pihkin, E., et al., J Biomed Mater Res 90A: 1137-1151 (2009). (Year: 2009).*
Polini, A., et al., PLoS ONE 6(10): e26211 (2011). (Year: 2011).*
Furtos, G., et al., J Biomed Mater Res Part B, 105B: 966 â 976 (2017). (Year: 2017).*
First Office Action mailed Feb. 4, 2023 in connection with Chinese Patent Application No. 202211015904.2, 12 pgs. (including translation).
Second Office Action mailed Mar. 15, 2023 in connection with Chinese Patent Application No. 202211015904.2, 13 pgs. (including translation).

* cited by examiner

*Primary Examiner* — David J Blanchard
*Assistant Examiner* — Daniel F Coughlin
(74) *Attorney, Agent, or Firm* — Chiesa Shahinian & Giantomasi PC

(57) ABSTRACT

The present disclosure provides a fiber membrane and a preparation method and use thereof, and belongs to the field of biological materials. The fiber membrane includes a fiber with a core-shell structure, where a core of the fiber includes simvastatin and a first spinnable polymer, and a shell of the fiber includes hydroxyapatite and a second spinnable polymer. In the fiber, a release of the simvastatin mainly depends on a rate of water invasion. After water invades the fiber, the simvastatin in the fiber leaves the fiber with the diffusion of water. In the present disclosure, a barrier function of the shell prevents moisture from entering the core. Therefore, the simvastatin in the core cannot leave the fiber with the diffusion of water molecules in an early stage, and a release rate of drugs is slowed down in the early stage, thereby controlling sustained release of the drugs.

3 Claims, 2 Drawing Sheets

FIBER MEMBRANE AND PREPARATION METHOD AND USE THEREOF

CROSS REFERENCE TO RELATED APPLICATION

This application claims the benefit and priority of Chinese Patent Application No. 202211015904.2, filed Aug. 24, 2022; the disclosure of which is incorporated by reference herein in its entirety as part of the present application.

TECHNICAL FIELD

The present disclosure belongs to the field of biological materials, in particular to a fiber membrane and a preparation method and use thereof.

BACKGROUND

Trauma and infection caused by external factors lead to some defects in bone structures, forming large gaps called bone defects. Tens of millions of people worldwide suffer from the bone defects caused by infections and complications due to severe trauma and improper treatment annually. Although in recent years, active treatment measures have been adopted in an early stage of bone defect treatment, making the incidence of bone nonunion and bone defect been significantly reduced, bone injury is still a difficult clinical problem.

Currently, the bone defects are generally treated by autogenous bone graft, allogeneic bone graft, and artificial bone materials. The autologous bone graft has the best repair effect for treating bone defects, but excessive use of the patient's own bone may bring new trauma and complications. Although the allogeneic bone graft can overcome partial problems caused by the autologous bone graft, it is limited by the source of a donor and rejection. The artificial bone materials can theoretically overcome the inherent shortcomings of autologous or allogeneic bone by selecting suitable materials for customization according to properties of the bone. An ideal repair material for the bone defects needs to have desirable biocompatibility, such as no toxicity, no deformation, facilitation of cell adhesion and proliferation, no inflammatory response, and promotion of cell growth and differentiation; moreover, such a material is further required to have an acceleration effect on bone repair, such as osteoinductivity and bone regeneration.

Electrospinning is a common technique for bottom-up fabrication of nanofibers using high-voltage electrostatics to draw working fluids into filaments. During the electrospinning, drugs or other nanoparticles can be easily loaded into the nanofibers without changing inherent properties. Therefore, the electrospinning is generally used to prepare bone regeneration-promoting materials, with desirable clinical application prospects. The traditional preparation method of fiber materials is to mix raw materials and then conduct electrospinning. However, fiber materials prepared by this method cannot control release of the drugs, and are prone to initial burst release, thereby greatly affecting a use efficiency of the drugs during an entire treatment period.

SUMMARY

A purpose of the present disclosure is to provide a fiber membrane and a preparation method and use thereof. The fiber membrane can control the sustained release of drugs and can promote bone regeneration.

The present disclosure provides a fiber membrane, including a fiber with a core-shell structure, where a core of the fiber includes simvastatin and a first spinnable polymer, and a shell of the fiber includes hydroxyapatite and a second spinnable polymer.

Preferably, the first spinnable polymer and the second spinnable polymer each are one selected from the group consisting of polycaprolactone, polylactic acid, and a polylactic acid copolymer.

The present disclosure further provides a preparation method of the fiber membrane, including the following steps:

conducting coaxial electrospinning on a core spinning solution and a shell spinning solution to obtain the fiber membrane; where the core spinning solution includes the simvastatin and the first spinnable polymer; and the shell spinning solution includes the hydroxyapatite and the second spinnable polymer.

Preferably, the core spinning solution includes 5 g/L to 20 g/L of the simvastatin and preferably 100 g/L to 150 g/L of the first spinnable polymer by concentration.

Preferably, the shell spinning solution includes 5 g/L to 15 g/L of the hydroxyapatite and 70 g/L to 120 g/L of the second spinnable polymer by concentration.

Preferably, the core spinning solution and the shell spinning solution each are added at a flow rate of 0.1 mL/h to 2 mL/h.

Preferably, during the coaxial electrospinning, a spinning nozzle and a collector are spaced apart by 15 cm to 20 cm.

Preferably, the coaxial electrospinning is conducted at 25° C. to 40° C. with an environmental humidity of 40% to 50%.

Preferably, the coaxial electrospinning is conducted at a voltage of 7.5 kV to 8.5 kV.

The present disclosure further provides use of the fiber membrane or a fiber membrane prepared by the preparation method in preparation of a bone repair membrane.

The present disclosure provides a fiber membrane, including a fiber with a core-shell structure, where a core of the fiber includes simvastatin and a first spinnable polymer, and a shell of the fiber includes hydroxyapatite and a second spinnable polymer. In the fiber, a release of the simvastatin mainly depends on a rate of water invasion. After water invades the fiber, the simvastatin in the fiber leaves the fiber with the diffusion of water. In the present disclosure, a barrier function of the shell prevents moisture from entering the core. Therefore, the simvastatin in the core cannot leave the fiber with the diffusion of water molecules in an early stage, and a release rate of drugs is slowed down in the early stage, thereby controlling sustained release of the drugs. In addition, the hydroxyapatite in the shell can synergize with the simvastatin to promote bone regeneration. Experimental results of examples show that the fiber membrane of the present disclosure can continuously release the drugs for up to 28 d.

Further, the spinnable polymer is polycaprolactone that can improve biocompatibility of the fiber membrane.

DETAILED DESCRIPTION

Figure 1:
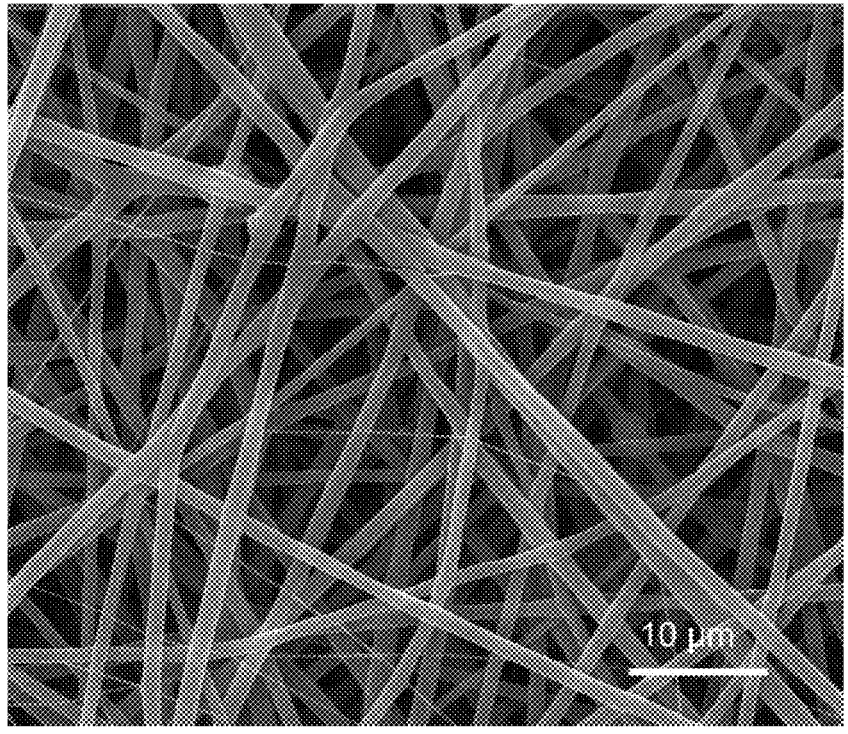
FIG. 1 shows a scanning electron microscopy (SEM) image of a fiber membrane prepared in Example 1 of the present disclosure.

The present disclosure provides a fiber membrane, including a fiber with a core-shell structure, where a core of the fiber includes simvastatin and a first spinnable polymer, and a shell of the fiber includes hydroxyapatite and a second spinnable polymer.

In the present disclosure, the first spinnable polymer and the second spinnable polymer each are preferably one selected from the group consisting of polycaprolactone, polylactic acid, and a polylactic acid copolymer. In the core, the simvastatin and the first spinnable polymer have a mass ratio of preferably 1:(5-30), more preferably 1:(10-20), and furthermore preferably 1:(15-18); and in the shell, the hydroxyapatite and the second spinnable polymer have a mass ratio of preferably 1:(4.7-24), more preferably 1:(5-20), and further more preferably 1:(10-15). The core and the shell have a mass ratio of preferably 1:(0.5-1), more preferably 1:(0.6-0.8). The fiber has an average diameter of preferably 0.36 μm to 1.57 μm, more preferably 0.41 μm to 1.57 μm, and furthermore preferably 0.63 μm to 1.57 μm. The shell has a thickness of preferably 47 nm to 172 nm, more preferably 58 nm to 172 nm, and furthermore preferably 74 nm to 172 nm.

In the fiber, a release of the simvastatin mainly depends on a rate of water invasion. After water invades the fiber, the simvastatin in the fiber leaves the fiber with the diffusion of water. In the present disclosure, a barrier function of the shell prevents moisture from entering the core. Therefore, the simvastatin in the core cannot leave the fiber with the diffusion of water molecules in an early stage, and a release rate of drugs is slowed down in the early stage, thereby controlling sustained release of the drugs. In addition, the hydroxyapatite in the shell can synergize with the simvastatin to promote bone regeneration.

The present disclosure further provides a preparation method of the fiber membrane, including the following steps:

conducting coaxial electrospinning on a core spinning solution and a shell spinning solution to obtain the fiber membrane; where the core spinning solution includes the simvastatin and the first spinnable polymer; and the shell spinning solution includes the hydroxyapatite and the second spinnable polymer.

In the present disclosure, the core spinning solution includes preferably 5 g/L to 20 g/L, more preferably 10 g/L to 18 g/L, and furthermore preferably 12 g/L to 16 g/L of the simvastatin and preferably 100 g/L to 150 g/L, more preferably 120 g/L to 140 g/L of the first spinnable polymer by concentration. The core spinning solution further includes preferably an organic solvent. The organic solvent is preferably hexafluoroisopropanol or chloroform. A preparation method of the core spinning solution includes preferably the following steps: mixing the simvastatin, the first spinnable polymer, and the organic solvent to obtain the core spinning solution. There is no special limitation on the mixing, as long as an obtained mixture can be clear and transparent using schemes well known to those skilled in the art. Specifically, in an example, the mixing is conducted by magnetic stirring at a room temperature for 6 h.

In the present disclosure, the shell spinning solution includes preferably 5 g/L to 15 g/L, more preferably 8 g/L to 12 g/L, and furthermore preferably 10 g/L to 11 g/L of the hydroxyapatite and preferably 70 g/L to 120 g/L, more preferably 80 g/L to 110 g/L, and further more preferably 90 g/L to 100 g/L of the second spinnable polymer by concentration. The shell spinning solution further includes preferably an organic solvent. The organic solvent is preferably hexafluoroisopropanol or chloroform. A preparation method of the shell spinning solution includes preferably the following steps: conducting first mixing on the second spinnable polymer and the organic solvent, and after an obtained mixed solution is clarified, conducting second mixing on the hydroxyapatite and the mixed solution to obtain the shell spinning solution. There is no special limitation on the first mixing and the second mixing, as long as the materials can be mixed uniformly by adopting schemes well known to those skilled in the art. Specifically, in an example, the first mixing and the second mixing each are conducted by magnetic stirring at a room temperature for 6 h. The shell spinning solution is preferably a suspension. The shell spinning solution is preferably prepared for immediate use. The preparation for immediate use can prevent settling of the hydroxyapatite due to an inability to be dissolved after a long time, and can also avoid the influence of long-term storage, illumination, temperature or other factors on the spinning solution, thereby improving a success rate of the fiber attaching to the hydroxyapatite.

In the present disclosure, the core spinning solution is added at a flow rate of preferably 0.1 mL/h to 2 mL/h, more preferably 1 mL/h to 1.5 mL/h; and the shell spinning solution is added at a flow rate of preferably 0.1 mL/h to 2 mL/h, more preferably 0.8 mL/h to 1 mL/h. During the coaxial electrospinning, a spinning nozzle and a collector are spaced apart by preferably 15 cm to 20 cm, more preferably 16 cm to 18 cm. The coaxial electrospinning is conducted at preferably 25° C. to 40° C., more preferably 30° C. to 35° C. with an environmental humidity of preferably 40% to 50%, more preferably 45% to 48%. The coaxial electrospinning is conducted at a voltage of preferably 7.5 kV to 8.5 kV, more preferably 8 kV to 8.2 kV. Preferably, when droplets at the spinning nozzle of the coaxial electrospinning are gradually formed and stabilized, the voltage of the coaxial electrospinning is slowly increased to 7.5 kV to 8.5 kV; after an entire electrospinning process is stable, a new collector is replaced to start collecting the fiber with a core-shell structure. There is no special limitation on the collector, and collectors known to those skilled in the art can be selected. Specifically, in an example, the collector is an aluminum foil or a copper mesh.

In the present disclosure, before the coaxial electrospinning, the core spinning solution and the shell spinning solution are preferably loaded into two syringes and then placed on two propelling pumps, respectively. The plastic syringe containing the shell spinning solution and the spinning nozzle are directly connected, while the plastic syringe containing the core spinning solution and the spinning nozzle are connected by a hose; during the coaxial electrospinning, the shell spinning solution and the core spinning solution are simultaneously ejected from the nozzle.

In the present disclosure, after the coaxial electrospinning is completed, an obtained product is preferably dried to obtain the fiber membrane. There is no special limitation on the drying, as long as the organic solvent can be removed by schemes well known to those skilled in the art. Specifically, in an example, the drying is conducted at 40° C. for 48 h in a constant-temperature drying oven.

The present disclosure further provides use of the fiber membrane or a fiber membrane prepared by the preparation method in preparation of a bone repair membrane.

In order to further illustrate the present disclosure, the fiber membrane and the preparation method and the use thereof provided by the present disclosure are described in detail below with reference to the accompanying drawings and examples, but the accompanying drawings and the examples should not be construed as limiting the protection scope of the present disclosure.

Example 1

0.7 g of polycaprolactone was added to a 30 mL transparent glass bottle, and 10 mL of a hexafluoroisopropanol solution was pipetted into the glass bottle with a pipette; a magnetic rotor was added to the glass bottle and a bottle cap was tightened, and a resulting mixture in the glass bottle was stirred in a magnetic stirrer at a room temperature for 6 h. After an obtained solution was clarified, the bottle cap was unscrewed, 0.05 g of a hydroxyapatite powder was added, the bottle cap was tightened, and a mixture in the bottle was magnetically stirred for 6 h to obtain a white suspension as a shell spinning solution.

1.0 g of the polycaprolactone and 0.05 g of simvastatin were added to a 30 mL transparent glass bottle, and 10 mL of the hexafluoroisopropanol solution was pipetted into the glass bottle with a pipette; a magnetic rotor was added to the glass bottle and a bottle cap was tightened, and a resulting mixture in the glass bottle was stirred in a magnetic stirrer at a room temperature for 6 h to obtain a transparent and clear core spinning solution. The core and the shell had a mass ratio of 0.71:1.

The shell spinning solution and the core spinning solution were added into two 10 mL syringes and then placed on different propelling pumps, respectively; the syringe containing the shell spinning solution and the spinning nozzle were directly connected, while the syringe containing the core spinning solution and the spinning nozzle were connected by a silicone hose. The propellant pumps were turned on, and the shell spinning solution and the core spinning solution flowed out from the spinning nozzle at flow rates of 1.0 mL/h and 1.5 mL/h, respectively. At 30° C. with an environmental humidity of 45%, a voltage of coaxial electrospinning was slowly applied to 7.5 kV, and the spinning nozzle and an aluminum foil had a spacing of 15 cm; after receiving for 2 h, a received product was dried in a constant-temperature drying oven at 40° C. for 48 h to obtain a fiber membrane. In Example 1, the fiber had an average diameter of 0.63 μm to 1.57 μm and a shell thickness of 74 nm to 172 nm.

Example 2

0.6 g of polycaprolactone was added to a 30 mL transparent glass bottle, and 10 mL of a hexafluoroisopropanol solution was pipetted into the glass bottle with a pipette; a magnetic rotor was added to the glass bottle and a bottle cap was tightened, and a resulting mixture in the glass bottle was stirred in a magnetic stirrer at a room temperature for 6 h. After an obtained solution was clarified, the bottle cap was unscrewed, 0.05 g of a hydroxyapatite powder was added, the bottle cap was tightened, and a mixture in the bottle was magnetically stirred for 6 h to obtain a white suspension as a shell spinning solution.

1.0 g of the polycaprolactone and 0.05 g of simvastatin were added to a 30 mL transparent glass bottle, and 10 mL of the hexafluoroisopropanol solution was pipetted into the glass bottle with a pipette; a magnetic rotor was added to the glass bottle and a bottle cap was tightened, and a resulting mixture in the glass bottle was stirred in a magnetic stirrer at a room temperature for 6 h to obtain a transparent and clear core spinning solution. The core and the shell had a mass ratio of 0.62:1.

The shell spinning solution and the core spinning solution were added into two 10 mL syringes and then placed on different propelling pumps, respectively; the syringe containing the shell spinning solution and the spinning nozzle were directly connected, while the syringe containing the core spinning solution and the spinning nozzle were connected by a silicone hose. The propellant pumps were turned on, and the shell spinning solution and the core spinning solution flowed out from the spinning nozzle at flow rates of 1.0 mL/h and 1.5 mL/h, respectively. At 30° C. with an environmental humidity of 45%, a voltage of coaxial electrospinning was slowly applied to 7 kV, and the spinning nozzle and an aluminum foil had a spacing of 15 cm; after receiving for 2 h, a received product was dried in a constant-temperature drying oven at 40° C. for 48 h to obtain a fiber membrane. In Example 2, the fiber had an average diameter of 0.41 μm to 1.34 μm and a shell thickness of 58 nm to 160 nm.

Example 3

0.5 g of polycaprolactone was added to a 30 mL transparent glass bottle, and 10 mL of a hexafluoroisopropanol solution was pipetted into the glass bottle with a pipette; a magnetic rotor was added to the glass bottle and a bottle cap was tightened, and a resulting mixture in the glass bottle was stirred in a magnetic stirrer at a room temperature for 6 h. After an obtained solution was clarified, the bottle cap was unscrewed, 0.05 g of a hydroxyapatite powder was added, the bottle cap was tightened, and a mixture in the bottle was magnetically stirred for 6 h to obtain a white suspension as a shell spinning solution.

1.0 g of the polycaprolactone and 0.05 g of simvastatin were added to a 30 mL transparent glass bottle, and 10 mL of the hexafluoroisopropanol solution was pipetted into the glass bottle with a pipette; a magnetic rotor was added to the glass bottle and a bottle cap was tightened, and a resulting mixture in the glass bottle was stirred in a magnetic stirrer at a room temperature for 6 h to obtain a transparent and clear core spinning solution. The core and the shell had a mass ratio of 0.52:1.

The shell spinning solution and the core spinning solution were added into two 10 mL syringes and then placed on different propelling pumps, respectively; the syringe containing the shell spinning solution and the spinning nozzle were directly connected, while the syringe containing the core spinning solution and the spinning nozzle were connected by a silicone hose. The propellant pumps were turned on, and the shell spinning solution and the core spinning solution flowed out from the spinning nozzle at flow rates of 1.0 mL/h and 1.5 mL/h, respectively. At 30° C. with an environmental humidity of 45%, a voltage of coaxial electrospinning was slowly applied to 8.5 kV, and the spinning nozzle and an aluminum foil had a spacing of 15 cm; after receiving for 2 h, a received product was dried in a constant-temperature drying oven at 40° C. for 48 h to obtain a fiber membrane. In Example 3, the fiber had an average diameter of 0.36 μm to 1.29 μm and a shell thickness of 47 nm to 143 nm.

Comparative Example 1

1.0 g of polycaprolactone and 0.05 g of simvastatin were added to a 30 mL transparent glass bottle, and 10 mL of the hexafluoroisopropanol solution was pipetted into the glass bottle with a pipette; a magnetic rotor was added to the glass bottle and a bottle cap was tightened, and a resulting mixture in the glass bottle was stirred in a magnetic stirrer at a room temperature for 6 h to obtain a transparent and clear spinning solution.

The spinning solution was loaded into a 10 ml syringe and placed in a propelling pump at a propelling rate of 1.0 ml/h, and electrospinning was conducted at 30° C. with an environmental humidity of 45%, and a voltage of 6.5 kV, where the spinning nozzle and an aluminum foil had a spacing of 15 cm; and a fiber product was received for 2 h. The received fiber product was dried in a constant-temperature drying oven at 40° C. for 48 h to obtain a fiber membrane. The single-structured polycaprolactone drug fiber prepared by the traditional method was used as a comparative sample, and then a drug release test was conducted.

Figure 2:
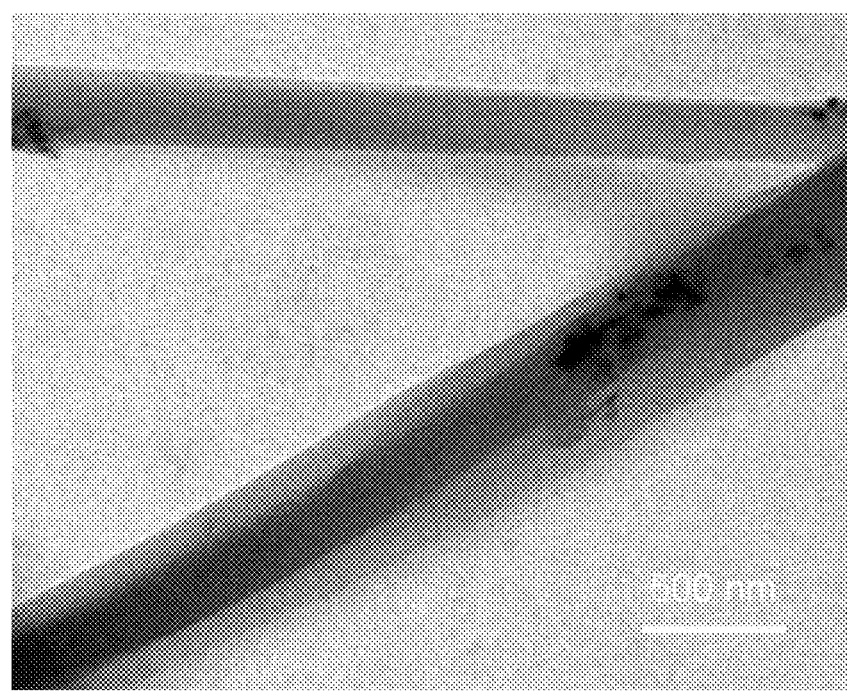
FIG. 2 shows a transmission electron microscopy (TEM) image of the fiber membrane prepared in Example 1 of the present disclosure.
Figure 3:
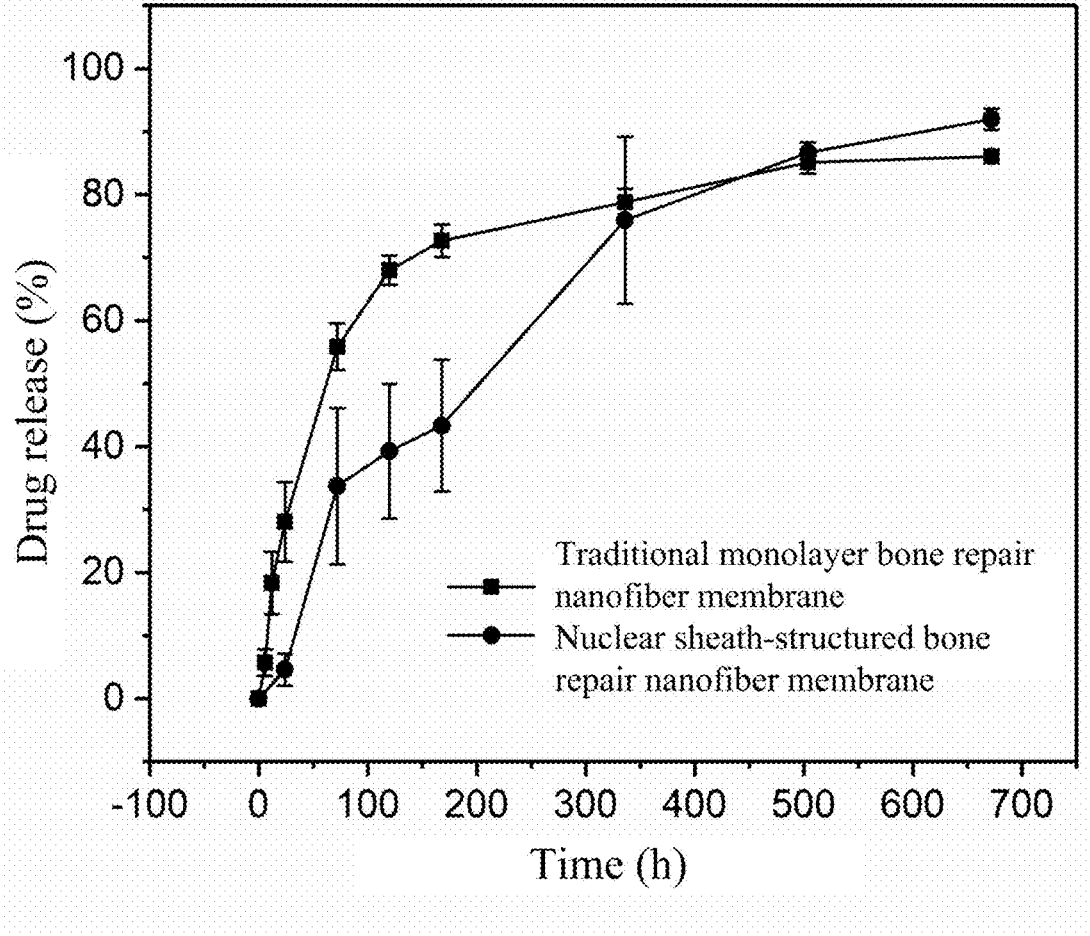
FIG. 3 shows drug release curves of the fiber membranes prepared in Example 1 and Comparative Example 1 of the present disclosure.

Performance Testing
  (1) The prepared fiber membrane was cut off with the aluminum foil, and fixed on a SEM sample stage with a conductive glue; under the protection of nitrogen, a surface of the fiber membrane sample was sprayed with gold to give the fiber membrane conductivity; and the fiber membrane sample was analyzed by SEM. The results were shown in FIG. 1. It was seen from FIG. 1 that in the fiber membrane prepared in Example 1, the fibers had a cylindrical shape and no adhesion; in addition, as shown in FIG. 1, there were granular protrusions in some fibers, which were presumed to be the hydroxyapatite in the shell.
  (2) The fiber membrane prepared by the present disclosure was received by a copper mesh, and double distilled water was added dropwise on the copper mesh to enhance a bonding force between the copper mesh and the fibers. After a surface of the copper mesh was naturally air-dried, an internal structure of the fiber sample was explored by TEM. The results were shown in FIG. 2. It was seen from FIG. 2 that the fibers exhibited a clear core-shell structure inside, and dark particles appeared on the surface of the fibers, confirming that the hydroxyapatite was located in the shell of the fiber membrane in FIG. 1.
  (3) Drug release tests were conducted on the fiber membranes prepared in Example 1 and Comparative Example 1 using a pulp method test in a 2015 version of the Chinese Pharmacopoeia: 0.2 g of the fiber membrane was placed in 900 mL of a PBS buffer in a 1 L beaker; at a preset time interval, an appropriate amount of an obtained solution was added with an equal amount of the solution, and an absorbance test was conducted on the solution sample by an ultraviolet spectrometer. The results were shown in FIG. 3. It was seen from FIG. 3 that the fiber membrane prepared by the present disclosure had a desirable drug sustained-release ability, which could continuously release the simvastatin for up to 28 d.

The repair cycle of bone defects depends on the degree of damages, resulting in different treatment cycles, generally ranging from 4 to 12 weeks. In the present disclosure, due to a long-term sustained-release ability of the drugs, the fiber membrane can promote bone regeneration in a previous month, and continue to induce recovery of the bone defects in subsequent stages using hydroxyapatite and biodegradable polycaprolactone loaded on the fiber shell. This material design can promote the treatment of bone defects through sustained-release of the simvastatin and long-term bone repair physically induced by the hydroxyapatite.

Although the present disclosure is described in detail in conjunction with the foregoing examples, they are only a part of, not all of, the examples of the present disclosure. Other examples can be obtained based on these examples without creative efforts, and all of these examples shall fall within the protection scope of the present disclosure.

What is claimed is:

1. A preparation method of a fiber membrane, the fiber membrane comprising a fiber with a core-shell structure, wherein a core of the fiber comprises simvastatin and a first spinnable polymer, and a shell of the fiber comprises hydroxyapatite and a second spinnable polymer, the method comprising the following steps:
  conducting coaxial electrospinning on a core spinning solution and a shell spinning solution to obtain the fiber membrane; wherein
  the core spinning solution comprises the simvastatin and the first spinnable polymer;
  the shell spinning solution comprises the hydroxyapatite and the second spinnable polymer,
  the first spinnable polymer and the second spinnable polymer each are polycaprolactone,
  wherein the core spinning solution comprises 5 g/L to 20 g/L of the simvastatin and 100 g/L to 150 g/L of the first spinnable polymer by concentration;
  the coaxial electrospinning is conducted at a voltage of 7.5 kV to 8.5 kV with a spinning nozzle and a collector spaced apart by 15 cm;
  the core spinning solution is added at a flow rate of 1.5 mL/h, and the shell spinning solution is added at a flow rate of 1.0 mL/h; and
  the core spinning solution comprises an organic solvent including hexafluoroisopropanol, wherein the core spinning solution is prepared by mixing the simvastatin, the first spinnable polymer, and the organic solvent.

2. The preparation method according to claim 1, wherein the shell spinning solution comprises 5 g/L to 15 g/L of the hydroxyapatite and 70 g/L to 120 g/L of the second spinnable polymer by concentration.

3. The preparation method according to claim 1, wherein the coaxial electrospinning is conducted at 25° C. to 40° C. with an environmental humidity of 40% to 50%.

\* \* \* \* \*